(12) United States Patent
Beuker et al.

(10) Patent No.: US 7,123,779 B2
(45) Date of Patent: Oct. 17, 2006

(54) METHOD AND APPARATUS FOR MERGING IMAGES INTO A COMPOSITE IMAGE

(75) Inventors: Rob Anne Beuker, Eindhoven (NL); Marcel Breeuwer, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 418 days.

(21) Appl. No.: 09/867,892

(22) Filed: May 30, 2001

(65) Prior Publication Data

US 2002/0018589 A1 Feb. 14, 2002

(30) Foreign Application Priority Data

Jun. 2, 2000 (EP) .................................. 00201955

(51) Int. Cl.
*G06K 9/36* (2006.01)
(52) U.S. Cl. ...................... 382/294; 382/284; 382/295; 382/293
(58) Field of Classification Search ................ 382/276, 382/284, 293–295, 132, 287; 345/629–641
See application file for complete search history.

(56) References Cited

U.S. PATENT DOCUMENTS

| | | | | |
|---|---|---|---|---|
| 5,430,806 A | * | 7/1995 | Nettles | 382/295 |
| 5,706,416 A | * | 1/1998 | Mann et al. | 345/427 |
| 5,923,791 A | * | 7/1999 | Hanna et al. | 382/295 |
| 6,078,699 A | * | 6/2000 | Lobregt et al. | 382/284 |
| 6,504,569 B1 | * | 1/2003 | Jasinschi et al. | 348/43 |
| 6,535,650 B1 | * | 3/2003 | Poulo et al. | 382/284 |

OTHER PUBLICATIONS

Schultz et al., 1999, IEEE International Conference on Acoustics, Speech and Signal Processing, vol. 4, pp. 3265-3268.

* cited by examiner

*Primary Examiner*—Bhavesh M. Mehta
*Assistant Examiner*—Patrick Edwards

(57) ABSTRACT

Merging of overlapping two-dimensional (2D) images that are formed by an image pick-up device as projections of a three-dimensional (3D) scene includes image registration by projective transformation of one of the 2D images. The transformation is derived from corresponding feature points found in both images. In order to achieve improved accuracy and stability, the coordinates of the corresponding feature points are translated so that, on average, the numerical ranges of coordinate values are minimized. An apparatus for performing the merging of overlapping 2D images includes an appropriately configured image processor or computer with an attached image acquisition device. In one embodiment, the apparatus is a diagnostic x-ray apparatus.

6 Claims, 4 Drawing Sheets

METHOD AND APPARATUS FOR MERGING IMAGES INTO A COMPOSITE IMAGE

BACKGROUND OF THE INVENTION

1. Field of the Invention

The present invention relates to image processing, in particular to methods and apparatus for registration and merging of a plurality of overlapping two-dimensional (2D) images of three-dimensional (3D) scenes, especially in cases where the 2D images are related to the 3D scenes by a projective (or camera) transformation. The invention also relates to apparatus for performing the disclosed image processing.

2. Description of the Related Art

In many fields of art and technology imaging of scenes that are too extended to be captured in a single camera image is important. Composite images of such scenes must be merged from individual overlapping images of more limited fields of view. One example of where image composition is useful is the formation of an image of an extended scene from the limited fields of view of a digital camera suitable for a PC. Another example is the formation of an image of an extended region of a patient from individual x-ray images which are usually of more limited fields of view.

In many cases, such as in the previous two examples, since individual 2D images are related to the 3D scene by projective transformations, pairs of the individual images to be merged are also related to each other by projective transformations. Consequently, as part of the image merging process, it is important to identify the best projective transformation relating each pair of overlapping 2D images so that by use of this transformation the images of the pair can be brought into registration.

Accordingly, methods have been developed and are known for determining such projective transformations. Typical of these methods is that disclosed in Schultz et al., 1999, *IEEE International Conference on Acoustics, Speech and Signal Processing*, vol. 4, pp. 3265–3268. Here, much attention is paid to automatically determining a plurality of pairs of corresponding points, one point of each pair being in each image, that is typically input in order to find the parameters of the projective transformation relating the images. Once the pairs of corresponding points in the two image are identified, actual determination of the projective transformation is disclosed to be routine.

However, merely routine determination of a projective transformation from a plurality of pairs of corresponding points has been discovered to often not be sufficiently stable or accurate. The relevant arts need a simple and accurate method of determining such projective transformations.

Citation of a reference herein, or throughout this specification, is not intended to be construed as an admission that such reference is prior art to the Applicant's invention of the invention subsequently claimed.

SUMMARY OF THE INVENTION

The objects of the present invention are to provide apparatus and methods which simply and stably determine an accurate projective transformation relating two images from pairs of corresponding points identified in each image of the pair.

Achieving these objects by the present invention depends on the discovery that a projective transformation can be better determined from a plurality of pairs of corresponding points in both images when the numerical ranges of the coordinates of these corresponding points are minimized. With minimum numerical ranges of the coordinates, errors arising from non-linear terms in the coordinates are reduced in comparison with other methods which are ignorant of this discovery.

The present invention minimizes these coordinate ranges prior to determining the projective transformation relating a pair of images. In one alternative, an original coordinate system is chosen in each image in advance to minimize these coordinate ranges. This choice can be made, for example, by finding a coordinate origin for which the sum of the radius vectors to the feature points is a minimum. Such a coordinate origin can be found by a search technique. In this alternative, the projective transformation is determined directly in the original coordinate system.

In another preferred alternative, an arbitrary original coordinate system is chosen in each image. Later, a translation vector is determined so that in a translated coordinate system the numerical coordinate ranges are minimized. Such a translation vector can be determined, for example, as the average of coordinates of all the corresponding points in each image. In this alternative, the projective transformation is first determined in the translated coordinate system, and then adjusted to apply in the original, untranslated coordinate system.

In either alternative, once the projective transformation relating the two images of a pair of images is determined, it is applied to bring the pair of images into spatial registration, or alignment. The spatially registered, or aligned, images can then be easily merged by superimposition, interpolation, resampling, or so forth.

The apparatus of this invention is configured to acquire a plurality of images and to carry out image merging according to the above methods. First, it can include any image acquisition apparatus that forms two-dimensional (2D) digital images by projection of a three-dimensional (3D) scene. Such image acquisition includes optical cameras of all sorts. It also includes, for example, x-ray apparatus that project an image of an object to be examined onto an x-ray image detection device. Also, images can simply be acquired over a communication link from remote image acquisition devices or image storage devices.

Second, the actual image processing can be performed by a suitably programmed general purpose computer, such as a PC. Alternately, it can be performed by specialized hardware adapted to image processing In detail, these objects are achieved by the following embodiments of this invention. In a first embodiment, the present invention includes a method for merging a pair of overlapping two-dimensional (2D) images, said images being projections of a single three-dimensional (3D) scene, said method comprising: selecting at least four feature points in the 3D scene, finding the 2D coordinates of the points in both images corresponding to the selected feature points, the 2D coordinates being found with respect to original coordinate systems in the two images, translating the original coordinate systems of the two images in order to substantially minimize the average coordinate ranges of the 2D coordinates found, determining the parameters of a substantially optimal projective transformation relating the corresponding translated coordinates in the two images, determining the parameters of the projective transformation for application in the non-translated coordinate systems of the two images, and merging the two images by transforming one image according to the projective transformation and combining the transformed image with the other image.

In a second embodiment, the invention includes an apparatus for merging a pair of overlapping two-dimensional (2D) images, said images being projections of a single three-dimensional (3D) scene, said apparatus comprising: means for obtaining a pair of 2D images, a processor responsive to the means for obtaining images and configured to perform the methods of the first embodiment, and a display for viewing the pair of images merged by the processor.

In a third embodiment, the invention includes an x-ray apparatus for merging a pair of overlapping two-dimensional (2D) images, said images being projections of a single three-dimensional (3D) scene, said apparatus comprising: an x-ray source for projecting a beam of x-rays through an object to be examined, an x-ray detector for obtaining digital x-ray images which are projections of the object, a processor responsive to pairs of overlapping x-ray images obtained by the x-ray detector and configured to perform the methods of the first embodiment, and a display for viewing the pair of images merged by the processor.

In a fourth embodiment, the invention includes a computer readable medium comprising encoded program instructions for causing a processor to perform the methods of the first embodiment.

BRIEF DESCRIPTION OF THE DRAWING

Other objects, features and advantages of the present invention will become apparent upon perusal of the following detailed description when taken in conjunction with the appended drawing, wherein.

DETAILED DESCRIPTION OF THE PREFERRED EMBODIMENTS

In the following, exemplary embodiments of apparatus for practicing the present invention are first described followed by detailed descriptions of preferred embodiments of the methods of the present invention.

Preferred Apparatus of the Invention

Figure 1:
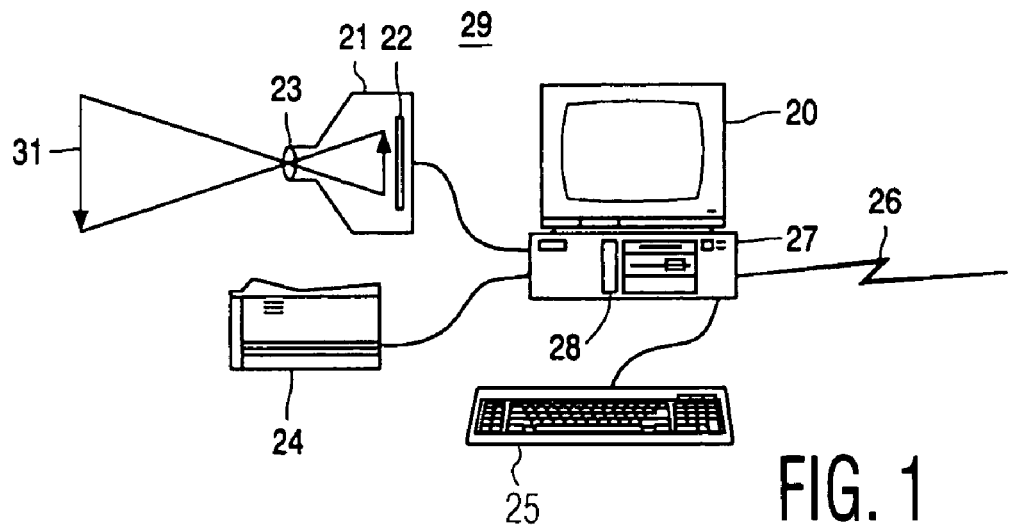
FIG. 1 illustrates a system for practicing the invention.

The present invention is preferably practiced on apparatus capable of appropriate processing two-dimensional digital (2D) images. FIG. 1 illustrates exemplary PC-type computer apparatus 29 equipped for appropriate image processing. This apparatus includes PC-type computer 27 having a microprocessor for computing and image processing. PC 27 can also optionally include special image-processing board 28, or other similar hardware, for assisting or entirely performing certain image processing functions. A user employs keyboard 25 and other input devices to control the image processing according to this invention. Original and processed images can be displayed on monitor 20 or printed on hardcopy output device 24. Original and processed images can also be transferred over network link 26.

Digital 2D images of 3D scenes can be obtained for input to the apparatus of this invention for processing by the methods of the present invention by any means known in the art. One exemplary means is to simply scan standard photographs with a digital scanner. FIG. 1 illustrates another exemplary means, digital PC camera 21 which includes lens system 23 for optical imaging and CCD array 22 for conversion of an optical image to digital signals for input to PC 27. As illustrated, an image of a 3D scene including arrow 31 is projected onto COD array 22 through lens system 23.

Figure 2:
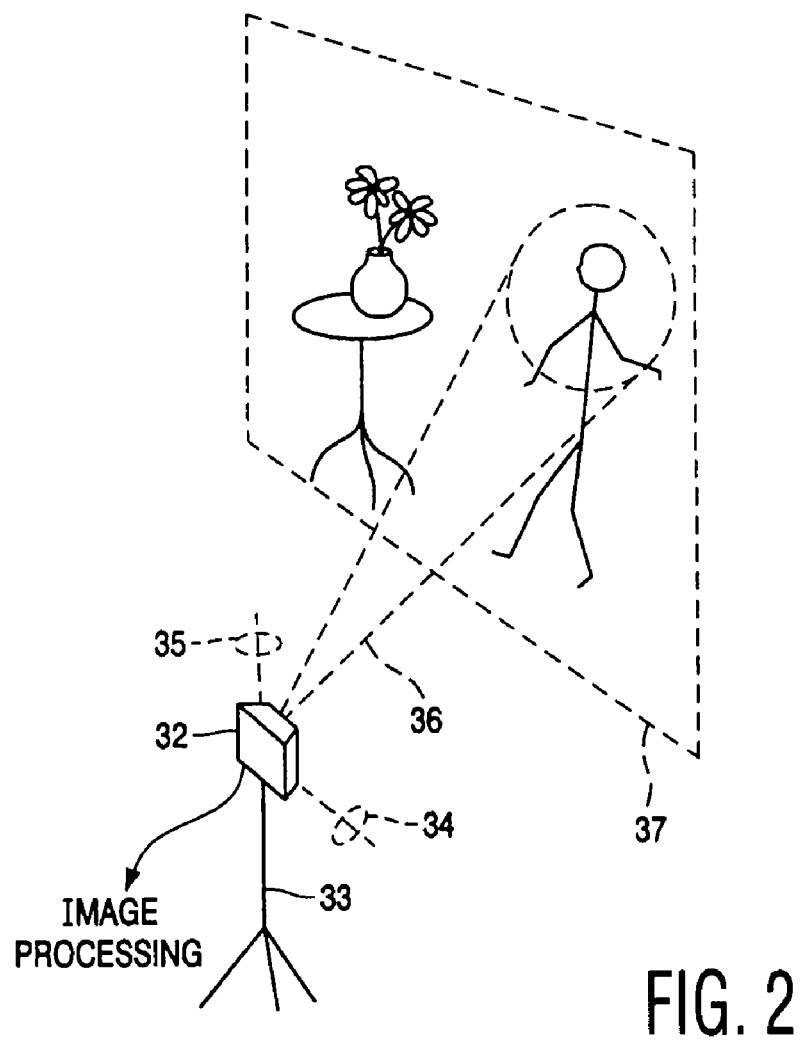
FIG. 2 illustrates an optical device for obtaining images to be processed in the invention.

FIG. 2 illustrates use of digital camera 32, perhaps of greater capability than PC camera 21, which is mounted on tripod 33 for rotation about axes 34 and 35 in order to pan across extended scene 37. Since camera 32 can form images of only a limited part of the 3D scene at one time, for example, of objects in cone 36 which is projected onto a digital pickup in camera 32, forming an image of entire extended scene 37 requires that multiple individual images be merged into a composite image by the image processing apparatus according to the present invention. Digital camera 32 can be responsive to selected bands of electromagnetic radiation, for example to infrared or to visible light.

Figure 3:
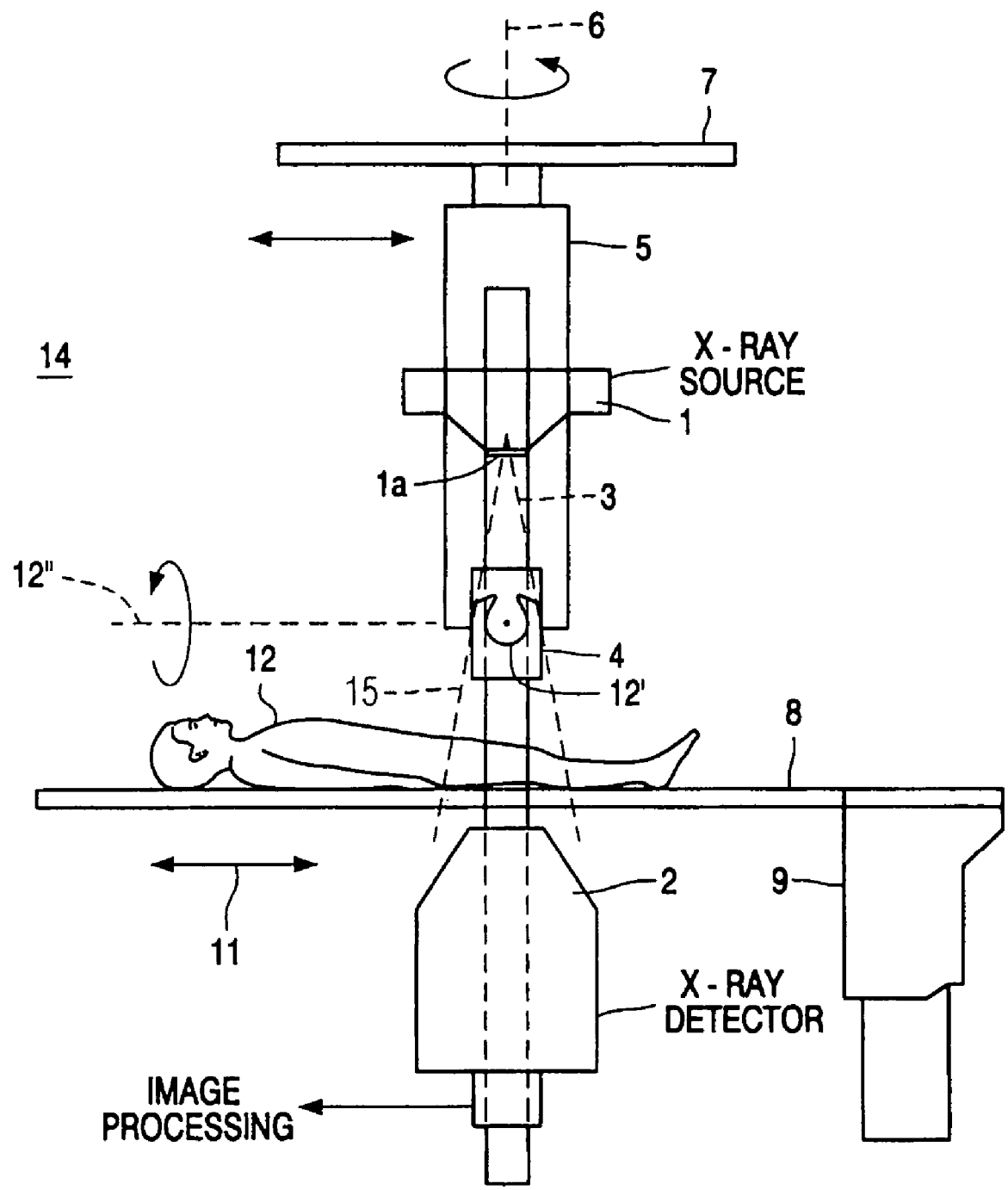
FIG. 3 illustrates a diagnostic x-ray device for obtaining images to be processed in the invention.

The need to merge multiple overlapping images into a single composite image arises in many other fields of art and technology, for example in medical diagnostics. FIG. 3 illustrates x-ray imaging apparatus 14 which forms 2D projection images of 3D patient 12, or of other objects to be examined. This apparatus projects x-ray beam 15 from a focal point within x-ray source 1, through diaphragm 1a, then through patient 12 and finally onto x-ray detector 2 which outputs a digital image signal for input to an image processor configured according to the present invention. The parameters of the x-ray image projection change with motions of the x-ray source and x-ray detector along the various illustrated degrees of freedom.

For example, patient 12 can be longitudinally displaced along direction 11 on patient table 8 by motor means 9. The x-ray source and the x-ray detector, mounted on C-arm 3 that is in turn mounted by collar 4 on support 5, are capable of coordinated rotation about two perpendicular horizontal axes 12' and 12". Finally, support 5 can be longitudinally translated along rails 7 or rotated about vertical axis 6. The present invention is also applicable to x-ray apparatus with other means for jointly moving the x-ray source and the x-ray detector for rotation or translation.

Figure 4:
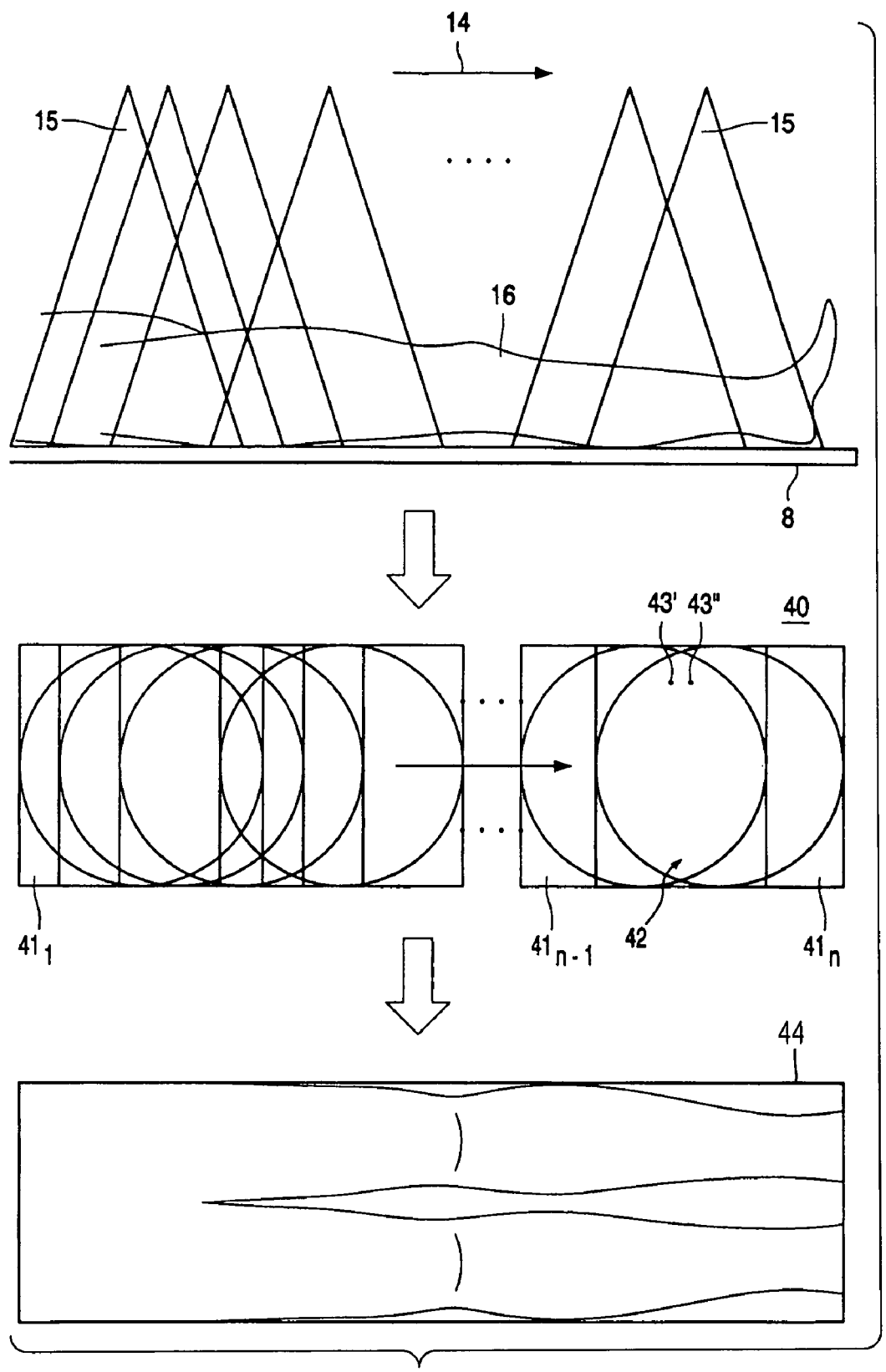
FIG. 4 illustrates image registration and merging for a plurality of diagnostic x-ray images.

To obtain a composite image of an extended region of the patient, for example, of the patient's legs, a plurality of individual images formed during panning of the x-ray apparatus about one or more of these degrees of freedom must be merged. FIG. 4 illustrates in a diagrammatic fashion the formation of limited images and the merging of consecutive and overlapping images into an assembled extended image. A patient's leg 16 is shown on patient table 8. Vertical support 5 is moved along rails 7, so that the x-ray source is moved in the direction of arrow 14. As the x-ray source is moved, x-ray beam 15 is intermittently directed at the patient's leg. Together with the x-ray sources the x-ray detector is also moved so as to face the x-ray source when the patient is irradiated. Whenever the patient's leg is irradiated, a limited x-ray image is formed on the entrance screen of the image intensifier. Thus, collection 40 is formed of consecutive images $41_1$ to $41_n$ which mutually overlap to various degrees. The overlap between sub-images depends on the displacement between positions of the x-ray source at the irradiation for forming said sub-images.

An apparatus configured according to the present invention accurately merges the sub-images of collection 40 into assembled image 44 which contains a shadow-image of the patient's entire legs. For example, images 41 n−1 and 41$_n$ need to be brought into spatial registration before merging, mis-registration being due, for example, to planned or accidental changes in the orientation of x-ray beam 15 when the two projection images are formed. Mis-registration is reflected in area 42 of overlap where, for example, point 43$_{n-1}$ is at a different location than point 43$_n$, although both points represent the same feature in patient leg 16. Mis-registration is corrected by determining a projective transformation that relates images 41$_{n-1}$ and 41$_n$ so that points 43$_{n-1}$ and 43$_n$ are at the same spatial position. Images in spatial registration can be merged without blurring.

Preferred Methods of the Invention

Having obtained a plurality of overlapping 2D images as projections of a 3D scene by any appropriate image acquisition device, for example, by the devices described above, appropriate image processing apparatus, for example, apparatus 29, programmed to perform the methods of this invention merges the overlapping individual images into a composite 2D image of the 3D scene.

Figure 5:
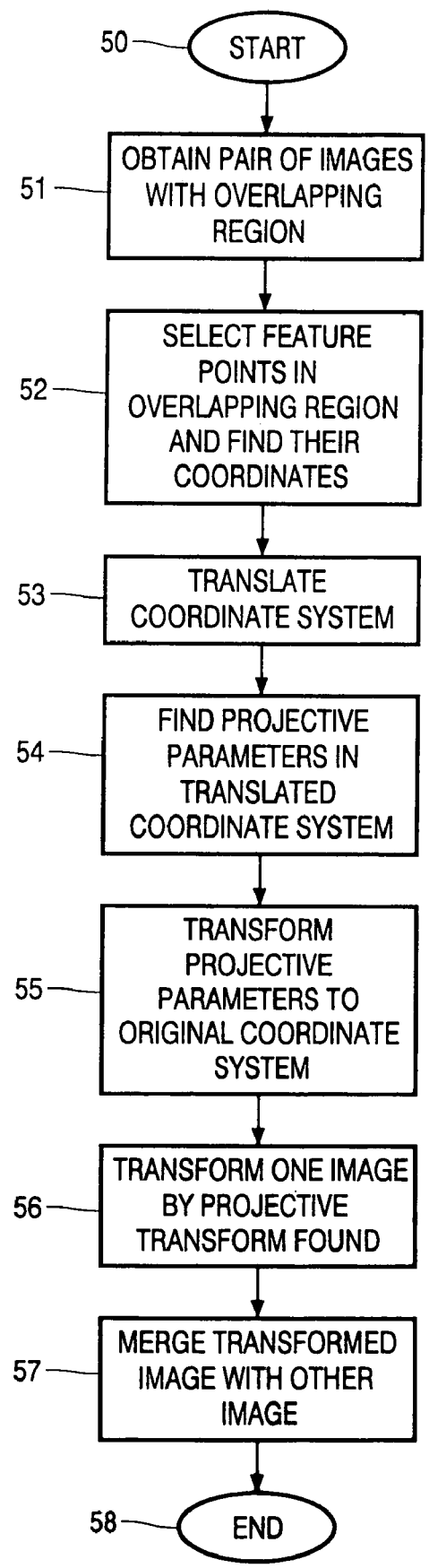
FIG. 5 illustrates an embodiment of the method according to the invention.

With reference to FIG. 5, for a pair of overlapping 2D images obtained at step 51, these methods generally perform the following steps: first at step 52, selection of feature points in the overlapping 2D region in each image that correspond to the same feature in the 3D scene; second at steps 53, 54, and 55, determination of a substantially optimal projective transformation relating the two individual images from the feature point coordinates; third at step 56, transformation of one image of the pair by the projective transformation; and fourth at step 57, merging the two images into a composite image. In the present invention, a substantially optimal projective transformation is one whose errors are due to any uncertainties in the input coordinate data and to any numerical errors arising in the method by which the transform is determined.

Where three or more image are to be merged, pairs of images can be selected and pairwise merged according to the methods of the invention by following any appropriate sequence assuming the necessary image overlaps are present. For example, the images can be merged sequentially by initially merging the first two images, then subsequently merging the third image with the result of merging first two images, and so forth. Alternatively, the images can be merged hierarchically by initially merging the first two images, then subsequently merging the second two images, then merging the previous two results, and so forth. Other appropriate merging sequences can be selected to match the structure of the original 3D scene.

Turning now to a more detailed description of the individual steps of the methods, selection of feature points in the overlapping region of a pair of overlapping 2D images at step 52 can, for example, be done manually. Here, a user, for example, at apparatus 29, selects N easily distinguishable points in the 3D scene that appear in both images. Then these feature points are identified in both images, and their coordinates are measured in both the images. This results in N pairs of 2D coordinates, each pair being the corresponding coordinates of a feature point. These are represented by the pairs:

$$u_i = (u_{1,i} u_{2,i})^T, v_i = (v_{1,i} v_{2,i})^T, i=1, \ldots, N \quad (1)$$

Here, the $u_i$ are the coordinates of points in one image, and the $v_i$ are the coordinates of corresponding points in the other image.

Alternatively, the feature points may be selected automatically by the image processing apparatus. One automatic method proceeds by first sparsely sampling points in the overlapping region of the image, then using matching or correlation of locally surrounding blocks of points to determine candidate pairs of sampled points that should correspond to the same 3D scene point, and finally retaining only those candidates pairs that have sufficient surrounding image structure for accurate block matching or correlation. See, e.g., Schultz et al., 1999, *IEEE International Conference on Acoustics, Speech and Signal Processing*, vol. 4, pp. 3265–3268.

Another automatic method proceeds by first constructing multiresolution decomposition of the images by self-similar discrete wavelet transforms, then selecting candidate image points having local maximums of the pixel-value gradient greater than a threshold where the pixel-value gradient is prominent at all resolutions, and finally retaining only those pairs of candidates points that have sufficiently cross-correlated locally surrounding blocks of points, and thereby that should correspond to the same feature in the 3D scene. The conditions imposed on the pixel-value gradient are to insure that there is sufficient image structure surrounding the candidate points for accurate cross-correlation.

The next steps determine a single substantially optimal projective transformation that relates the pairs of corresponding points in the overlapping region of two images. A projective transformation best models the relation between the pairs of overlapping images because, as detailed above, the images are obtained by devices that project a 3D scene onto the 2D images. A projective transformation linking pairs of corresponding points is represented by the following matrix equation.

$$v_i = \frac{A \cdot u_i + T}{C^T \cdot u_i + 1} \quad (2)$$

This transformation has the following matrix parameters (A, C, T) which are determined by their eight matrix elements.

$$A = \begin{pmatrix} a_{11} & a_{12} \\ a_{21} & a_{22} \end{pmatrix}, C = (c_1 \ c_2)^T, T = (t_1 \ t_2)^T \quad (3)$$

This transformation is selected to hold for all N pairs of corresponding 2D coordinates previously selected.

The following rearrangements develop an alternate, more compact, representation of these N relations. First, multiplying by $C^T \cdot u_i + 1$ leads to the following linear relations for the matrix elements.

$$a_{11}u_{1,i} + a_{12}u_{2,i} - c_1 u_{1,i} v_{1,i} - c_2 u_{2,i} v_{1,i} + t_1 = v_{1,i} \quad (4a)$$

$$a_{21}u_{1,i} + a_{22}u_{2,i} - c_1 u_{1,i} v_{2,i} - c_2 u_{2,i} v_{2,i} + t_2 = v_{2,i} \quad (4b)$$

The following matrix form is equivalent to these relations.

$$\begin{bmatrix} u_{1,i} & u_{2,i} & 0 & 0 & -u_{1,i}v_{1,i} & -u_{2,i}v_{1,i} & 1 & 0 \\ 0 & 0 & u_{1,i} & u_{2,i} & -u_{1,i}v_{2,i} & -u_{2,i}v_{2,i} & 0 & 1 \end{bmatrix} \cdot \begin{bmatrix} a_{11} \\ a_{12} \\ a_{21} \\ a_{22} \\ c_1 \\ c_2 \\ t_1 \\ t_2 \end{bmatrix} = \begin{bmatrix} v_1 \\ v_2 \end{bmatrix} \quad (5)$$

Letting P represent the 8×1 matrix of transformation parameters and letting $U_i$ and $V_i$ represent the remaining matrices in Eqn. 5, allows the following compact linear representations that determine parameter matrix P.

$$U_i \cdot P = V_i, i = 1, \ldots, \frac{N}{2} \quad (6)$$

$$\begin{bmatrix} U_1 \\ U_2 \\ \vdots \\ U_{\frac{N}{2}} \end{bmatrix} \cdot P = \begin{bmatrix} V_1 \\ V_2 \\ \vdots \\ V_{\frac{N}{2}} \end{bmatrix} \quad (7)$$

Referring again to FIG. 5 in the light of Eqns. 6 and 7, next at step 53 the origin of the coordinate system in the two images is translated, or shifted, by vectors $u_o$ and $v_o$, respectively, so that the following coordinate transformation obtains.

$$u_i' = u_i - u_0, \; v_i' = v_i - v_0 \quad (8)$$

It is an important discovery on which this invention in founded that the stability and accuracy of the solution for the parameter matrix, P, is considerably improved if the coordinate translations are chosen in order to minimize, on average, the numerical range of all the coordinates values of the corresponding feature points in each image. Such minimization is effective because it reduces computational errors in the terms involving the products of feature point coordinates appearing in the matrices $U_i$, these product terms being apparent in Equations 4A, 4b and 5.

Such a minimizing translation can be determined by any means that is apparent to one of skill in the art. The following three relations define easily computable minimizing translation vectors, $u_o$ and $v_o$, $$u_0 = \min(u_i), \; v_0 = \min(v_i) \quad (9a)$$

$$u_0 = \frac{1}{N}\sum_i u_i, \; v_0 = \frac{1}{N}\sum_i v_i \quad (9b)$$

$$u_0 = \frac{\min(u_i) + \max(u_i)}{2}, \; v_0 = \frac{\min(v_i) + \max(v_i)}{2} \quad (9c)$$

Choosing the one of Eqns. 9a, 9b or 9c that leads to the smallest average range of all the coordinates values of the corresponding feature points, or alternatively, choosing another translation that leads to an even smaller average coordinate range, all N coordinate pairs are shifted by the chosen translation.

In an alternative embodiment, this translation can be avoided in the original coordinate systems if the two images are chosen so that the numerical ranges of the feature point coordinates are initially minimized. This choice can be done by searching for optimum placement of the origins of the coordinate systems in the two images. This search for the coordinate origin can seek to minimize any of Eqations 9a, 9b or 9c, or another metric such as the mean square distance of the feature points from the coordinate origin. If the coordinate systems are so chosen, the projective transformation can be directly determined.

Returning to the preferred embodiment, after the coordinate translation, the matrices $U_i$ and $V_1$ are determined for Eqns. 6 or 7 in step 54 according to the prescription of Eqn. 5. Since there are 8 entries in the parameter matrix, P, to be determined and since two equations results from each coordinate pair (see Eqns. 4a and 4b), at least 4 coordinate pairs for 4 feature points are needed to determine P from Eqns. 6 or 7. If there are more than 4 feature points, as is preferable, Eqns. 6 or 7 are over determined. In either case, these equations can be solved by known methods of numerical analysis to determine the substantially optimal projective transformation in step 55. See, i.e., Press et al., 1993, *Numerical Recipes in C: The Art of Scientific Computing*, Cambridge Univ. Press. One alternative solution method is to use a standard least squares method. In this method, the parameter matrix entries are those which minimize the following squared error function.

$$\Phi = \sum_i \|U_i \cdot P - V_i\|^2 \quad (10)$$

In detail, actual matrix entries can be determined by differentiating Eqn. 10, setting the derivative to 0, and solving the resulting linear equations.

Another and preferred alternative solution method is to apply a Singular Value Decomposition (SVD) to the matrix $[U_1 \; U_2 \; \ldots \; U_{N/2}]^T$. This results in the following well-known decomposition.

$$[U_1 \; U_2 \; \ldots \; U_{N/2}]^T = R^T \cdot D \cdot Q \quad (11)$$

Here, R and Q are orthonormal matrices and D is the following diagonal matrix.

$$D = \begin{bmatrix} D_r & 0 \\ 0 & 0 \end{bmatrix} \text{ with } D_r = \text{diag}(d_1, \ldots, d_r) \quad (12)$$

Using these matrices, the parameter matrix, P can be directly determined by the following solution.

$$P = Q^T \cdot D^{-1} \cdot R \cdot \begin{bmatrix} V_1 \\ V_2 \\ \vdots \\ V_{\frac{N}{2}} \end{bmatrix} \quad (12a)$$

$$D^{-1} = \begin{bmatrix} D_r^{-1} & 0 \\ 0 & 0 \end{bmatrix} \text{ with } D^{-1} = \text{diag}(d_1^{-1}, \ldots, d_r^{-1}) \quad (12b)$$

Having determined in step 55 the projective transformation parameters in the translated coordinate system, in step 56 they must be altered so that the projective transformation can be applied in the original, untranslated coordinate system. This alteration can be immediately made according to the following relations, where A, T and C are the projective transformation parameters in the original coordinate system, A', T' and C' are the projective parameters in the translated coordinate system, and the coordinates $(u \; v)^T$ in the two coordinate systems are related by the translation vectors $(u_0 \; v_0)^T$.

$$C' = \frac{C}{1 - C^T \cdot U_0} \quad (13a)$$

-continued $$T' = v_0 + \frac{T - A \cdot u_0}{1 - C^T \cdot u_0} \quad (13b)$$

$$A' = \frac{A + v_0 \cdot C^T}{1 - C^T \cdot u_0} \quad (13c)$$

These relations insure that the following, which represents the equivalence of the original and translated projective transformations, is true.

$$\frac{A' \cdot (u_i - u_0) + T'}{C^T \cdot (u_i - u_0) + 1} + v_0 = \frac{A \cdot u_i + T}{C^T \cdot u_i + 1} \quad (14)$$

Finally, with the projective transformation expressed in the original, untranslated, coordinate system, the final step, step 57, of the method merges a composite image from the two images. In this step, first, one of the images is transformed by the determined projective transformation in order to bring the two images into spatial registration. Next, the composite image is formed in the non-overlapping regions from the transformed image and the other image separately, perhaps with resampling onto a new grid defining the composite image. In the overlapping region, the composite image is formed from a combination of the transformed image and of the other image, for example, by interpolating the values of the points of these images and resampling onto the new grid of the composite image.

The methods of this invention are readily implemented on image processing apparatus, for example, apparatus 29, by programming the above steps in an appropriate programming language, for example, C or FORTRAN. Initialization and termination activities of such programs occur in steps 50 and 58, respectively. Optionally, numerical algebra packages, such as LINPACK, can be used to routinely perform various ones of the above steps, such as necessary matrix multiplication, finding the SVD and so forth. One of skill in the art can readily and routinely perform such programming in view of the above description.

Computer instructions for controlling a microprocessor or an image processor which are generated from the resulting programs can be stored on computer readable media for loading into a memory to control the microprocessor of the image processor to carry out the methods of the present invention. Such computer readable media include magnetic media, optical media, and even transmission over network links.

EXAMPLE

The following example demonstrates the improved stability and accuracy achieved with the methods of this invention.

First, two 2D test images representing overlapping projections of a 3D test scene were created. These test images were created so that they are related by a projective transformation having the following parameters.

$$A = \begin{pmatrix} 1 & 0 \\ 0 & 1 \end{pmatrix}, C = (0 \; 0)^T \text{ and } T = (-50 \; -12)^T$$

Next, 27 feature points and their coordinates were determined in the overlapping region of the test images. The coordinate values are recorded in the following table.

TEST FEATURE POINT COORDINATES

| POINT | $U_{1i}$ | $U_{2i}$ | $V_{1i}$ | $V_{2i}$ |
|---|---|---|---|---|
| 1 | 71 | 35 | 21 | 23 |
| 2 | 67 | 42 | 17 | 30 |
| 3 | 66 | 44 | 16 | 32 |
| 4 | 70 | 37 | 20 | 24 |
| 5 | 63 | 48 | 13 | 36 |
| 6 | 77 | 34 | 27 | 22 |
| 7 | 75 | 40 | 25 | 28 |
| 8 | 79 | 31 | 29 | 19 |
| 9 | 60 | 52 | 10 | 40 |
| 10 | 78 | 32 | 28 | 20 |
| 11 | 77 | 30 | 27 | 18 |
| 12 | 71 | 47 | 21 | 35 |
| 13 | 71 | 48 | 21 | 36 |
| 14 | 66 | 68 | 16 | 46 |
| 15 | 69 | 62 | 19 | 40 |
| 16 | 75 | 12 | 25 | 71 |
| 17 | 71 | 16 | 21 | 81 |
| 18 | 71 | 18 | 21 | 51 |
| 19 | 79 | 56 | 29 | 43 |
| 20 | 77 | 52 | 27 | 40 |
| 21 | 78 | 51 | 28 | 38 |
| 22 | 74 | 41 | 23 | 31 |
| 23 | 76 | 38 | 26 | 26 |
| 24 | 68 | 48 | 18 | 36 |
| 25 | 71 | 19 | 21 | 36 |
| 26 | 76 | 37 | 26 | 25 |
| 27 | 67 | 49 | 17 | 26 |

Next, these pairs of corresponding coordinates were used to determine a substantially optimum projective transformation by the above-described methods but without the step of translating the coordinate system to minimize on average the numerical coordinate ranges of the corresponding points. This resulted in a projective transformation with the following parameters.

$$A = \begin{pmatrix} 0.5099 & 0.0001 \\ -0.1844 & 0.6193 \end{pmatrix},$$

$$C = (-0.0054 \; 0.0002)^T \text{ and } T = (-23.34 \; 5.92)^T$$

Clearly, the A and T matrices have considerable errors. This method, which is similar to the direct known methods, is of questionable accuracy.

Finally, a substantially optimum projective transformation was determined as above and including the step of translating the coordinate system to minimize on average the numerical coordinate ranges of the corresponding points. This resulted in a projective transformation with the following parameters.

$$A = \begin{pmatrix} 1.1047 & 0.0139 \\ 0.0214 & 0.0963 \end{pmatrix},$$

$$C = (-0.0009 \; 0.0006)^T \text{ and } T = (-56.20 \; -14.99)^T$$

Clearly, the A and T matrices as determined according to the present invention are of substantially improved accuracy. The methods of the present invention are certainly relatively superior to the known direct methods.

This comparison demonstrates the improvements achieved by the present invention.

All references cited herein are incorporated herein by reference in their entirety and for all purposes to the same extent as if each individual publication or patent or patent application was specifically and individually indicated to be incorporated by reference in its entirety for all purposes.

The invention claimed is:

1. A method for merging a pair of overlapping two-dimensional (2D) images, wherein the images comprise projections of a single three-dimensional (3D) scene, said method comprising:

selecting at least four feature points in the 3D scene within an overlapping region of the pair of 2D images, finding 2D coordinates of points in both images corresponding to the selected feature points, the 2D coordinates being found with respect to original coordinate systems in the two images, translating coordinates of the 2D coordinates found in the original coordinate systems of the two images by a chosen translation, wherein the translation is chosen to substantially minimize in a translated coordinate system, on average, numerical coordinate ranges of coordinate values of the 2D coordinates found, determining first projective transformation parameters of a substantially optimal projective transformation in the translated coordinate system relating corresponding translated coordinates of the 20 coordinates found in the two images, determining, as a function of the first projective transformation parameters, second projective transformation parameters of a projective transformation for application in the non-translated original coordinate systems of the two images, wherein determining the second projective transformation parameters comprises altering the first projective transformation parameters in the translated coordinate system using translation vectors, wherein the translation vectors ensure an equivalence of (i) the projective transformation in the original coordinate systems and (ii) the projective transformation in the translated coordinate system is true, and merging the two images into a single composite 2D image by (i) transforming one 2D image according to the projective transformation for application in the non-translated original coordinate systems of the two images into a transformed 2D image using the second projective transformation parameters and (ii) combining the transformed 2D image with the other 2D image.

2. The method of claim 1, wherein selecting comprises automatically selecting feature points with sufficient surrounding structure for accurately matching of the corresponding 2D coordinates in the two images.

3. The method of claim 1, wherein translating comprises determining a translation for each image as an average of the 2D coordinates in the respective image.

4. The method of claim 1, wherein determining the first projective transformation parameters of the substantially optimal projective transformation in the translated coordinate system comprises performing a singular value decomposition.

5. The method of claim 1, wherein determining the first projective transformation parameters of the substantially optimal projective transformation in the translated coordinate system comprises performing a minimization of an error function.

6. A computer program product comprising computer readable media having a set of instructions executable by a computer, the instructions being configured for merging a pair of overlapping two dimensional (2D) images that comprise projections of a single three-dimensional (3D) scene according to the method of claim 1.

* * * * *